United States Patent [19]

Renner

[11] 4,228,302
[45] Oct. 14, 1980

[54] PROCESS FOR PREPARING A METHYL-SUBSTITUTED BENZALDEHYDE

[75] Inventor: Carl A. Renner, Wilmington, Del.

[73] Assignee: E. I. DuPont de Nemours and Company, Wilmington, Del.

[21] Appl. No.: 71,281

[22] Filed: Aug. 30, 1979

Related U.S. Application Data

[62] Division of Ser. No. 001,930, Jan. 8, 1979.

[51] Int. Cl.² ............................................. C07C 51/26
[52] U.S. Cl. ................................................... 562/408
[58] Field of Search ....................................... 562/408

[56] References Cited

FOREIGN PATENT DOCUMENTS 571586 11/1958 Italy ........................................ 562/418
51-160233 12/1975 Japan ..................................... 562/418

Primary Examiner—Paul J. Killos

[57] ABSTRACT

Process for formylating an alkyl-substituted benzene using carbon monoxide and hydrogen chloride, in the presence of aluminum chloride catalyst, in a reaction mixture which includes chlorobenzene as a solvent, and process for oxidizing an alkyl-substituted benzaldehyde using oxygen, in the presence of an autoxidation initiator, in a reaction mixture which includes cyclohexanone as a reductant.

6 Claims, No Drawings

PROCESS FOR PREPARING A METHYL-SUBSTITUTED BENZALDEHYDE

This is a division, of application Ser. No. 001,930, filed Jan. 8, 1979.

DESCRIPTION

1. Technical Field

This invention relates to an improved process for preparing a methyl-substituted benzaldehyde which can be oxidized, if desired, to the corresponding benzoic acid.

An object of this invention is to provide a process for preparing a methyl-substituted benzaldehyde of higher purity and in higher yield than can normally be achieved by means of commonly used prior art processes. Another object is to provide an improved process for preparing a methyl-substituted benzoic acid from the corresponding benzaldehyde.

2. Background Art

Carbonylation (formylation) of aromatic compounds, including benzene and alkyl-substituted benzenes, to obtain the corresponding aldehydes is a well-known reaction. The use of carbon monoxide and hydrogen chloride in the presence of aluminum chloride with or without cuprous chloride was studied by Gattermann and Koch, Ber., 30, 1622 (1897), and this formylation reaction is well-known as the Gattermann-Koch reaction. This reaction has been extensively reviewed by Olah and Kuhn in "Friedel-Crafts and Related Reactions" edited by G. A. Olah, Volume III, Part 2, Interscience Publishers, 1964, pages 1153–1178. Solvents normally employed for the reaction include nitrobenzene, benzene (when a sufficiently low temperature is employed for the reaction), an excess of the aromatic compound to be formylated, and solvents commonly used in Friedel-Crafts reactions. Although the Gattermann-Koch reaction has been employed for the preparation of methyl-substituted benzaldehydes, including mesitaldehyde (German Patent 98706 (1898) and Gatterman, Ann., 347, 374–375 (1906)), it has not previously been known to employ chlorobenzene as a solvent to obtain an improved yield of the aldehyde of high purity.

Ketone-promoted oxidation of aromatic aldehydes is well-known, particularly the oxidation of p-tolualdehyde to p-toluic acid (British Patent 1,282,775 (1972) and Japan. Kokai 75,160,233 (Chem. Abstracts 84, 164458 (1976)). Catalyzed air-oxidation of mesitaldehyde to mesitoic acid has not previously been known.

DISCLOSURE OF INVENTION

For further comprehension of the invention, and of the objects and advantages thereof, reference may be made to the following description and to the appended claims in which the various novel features of the invention are more particularly set forth.

The present invention resides in an improved formylation process for preparing a methyl-substituted benzaldehyde by contacting and reacting, in a reaction mixture, at a temperature within the range about 0° to 120° C., the compound of the formula

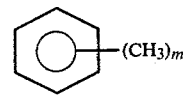

wherein m is 2, 3, 4 or 5, carbon monoxide, hydrogen chloride and aluminum chloride catalyst, with the methyl-substituted benzaldehyde thus produced being separated from the reaction mixture and recovered, the improvement characterized in that the formylation reaction is carried out in the reaction mixture in the presence of chlorobenzene as a solvent.

The invention also resides in an improved process for preparing a methyl-substituted benzoic acid by oxidizing, in a reaction mixture, at a temperature within the range about 0° to 120° C., the methyl-substituted benzaldehyde of the formula

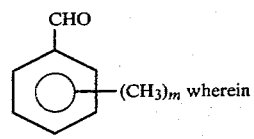 wherein m is 2, 3, 4 or 5, with an excess of oxygen, in the presence of about 0.01 to 2 percent by weight, based on the weight of aldehyde, of an autoxidation initiator, with the methyl-substituted benzoic acid thus produced being separated from the reaction mixture and recovered, the improvement characterized in that the oxidation reaction is carried out in the reaction mixture in the presence of at least 0.5 molar equivalent, per mole of aldehyde, of cyclohexanone as a reductant.

The process of the invention for the preparation of the methyl-substituted benzaldehyde employs chlorobenzene as a solvent for the formylation reaction. It has been discovered that the use of chlorobenzene gives a significant increase in yield and purity of the methyl-substituted benzaldehyde compared with the use of methylene chloride, dichloroethane or with no added solvent. Since the formation of side products is reduced when chlorobenzene is used, expensive purification procedures for the aldehyde are generally not required. It has also been discovered that oxidation of a methyl-substituted benzaldehyde to the corresponding methyl-substituted benzoic acid can be accomplished in good yield with oxygen in the presence of an autoxidation initiator and cyclohexanone (reductant). If desired, an excess of cyclohexanone can be used as a solvent for the reaction. The use of cyclohexanone gives an improved yield of product, compared with yields obtained in its absence. Replacement of cyclohexanone with such aliphatic ketones as acetone and 2-butanone is impractical and potentially hazardous because of the volatility of the latter compounds.

The formylation process of the invention is carried out by the Gattermann-Koch procedure, summarized by Olah and Kuhn, loc cit. The process is applicable to a variety of methyl-substituted benzene compounds of the aforesaid formula, including o-, m-, and p-xylene, 1,2,4-trimethylbenzene, 1,3,5-trimethylbenzene(mesitylene), 1,2,4,5-tetramethylbenzene(durene), 1,2,3,5-tetramethylbenzene and pentamethylbenzene. Mesitylene is a preferred compound.

An excess of carbon monoxide is generally employed in the formylation reaction, and at least about one mole of aluminum chloride per mole of substituted benzene is required for maximum yield. It is preferred to employ a smaller amount of hydrogen chloride, generally about 2 to 5 weight percent based on the substituted benzene, although larger amounts can be used.

A large excess of chlorobenzene can be employed as the solvent, but such an excess is not necessary to obtain the high yields of highly pure product. A convenient amount is 0.5 to 10 molar equivalents, preferably 1 to 5 molar equivalents, per mole of substituted benzene.

The reaction temperature of the formylation reaction can be within the range about 0° to 120° C. Since the reaction proceeds very slowly at 0° and product quality may be adversely affected at high temperatures, it is preferred to operate at temperatures of about 30° to 70° C.

Reaction pressures and reaction times are not critical. Since carbon monoxide and hydrogen chloride are gases, it is desirable to carry out the formylation reaction at elevated pressures, preferably at pressures of about 50 to 600 psi (350–4150 kPa). Reaction times can vary from a few minutes to several hours.

Oxidation of a methyl-substituted benzaldehyde to the corresponding methyl-substituted benzoic acid is carried out in the liquid phase with an excess of oxygen. Pure oxygen, air or other nitrogen/oxygen mixtures can be used for the oxidation reaction. The use of an autoxidation initiator increases the rate of reaction. Suitable initiators are those which initiate free-radical reactions and include azo initiators, e.g., azobisisobutyronitrile and azobisdimethylvaleronitrile; organic peroxides, e.g., benzoyl peroxide and di-tert-butyl peroxide; and metal salts of metals such as cobalt, manganese, vanadium, chromium, iron and nickel. Preferred initiators include cobalt salts, especially cobalt acetate. The amount of initiator employed is preferably about 0.01 to 2 percent by weight, based on the weight of methyl-substituted benzaldehyde.

Cyclohexanone is employed herein as a reductant in the aldehyde oxidation reaction. During the reaction the cyclohexanone is converted to caprolactone. The amount of cyclohexanone used is not critical so long as at least 0.5 molar equivalent, per mole of methyl-substituted benzaldehyde, is present. Preferably, at least one molar equivalent is present. An excess of cyclohexanone can be used as a solvent for the oxidation reaction, if desired.

Reaction temperature and time are not critical and reaction temperatures of about 0° to 120° C. are conveniently employed. A reaction temperature of about 30° to 70° C. is preferred. Reaction times can vary from less than one hour to several days or more, if the longer time is necessary to achieve completion of the reaction. In general, longer times are required at lower reaction temperatures.

Reaction pressure is not critical, and a pressure of about one atmosphere to 50 atmospheres (100–5100 kPa) or more is conveniently employed; preferably, about one to about 6 atmospheres (100–610 kPa). Since the oxygen reagent is gaseous, pressures of at least one atmosphere are usually employed.

Although a solvent is not required for the oxidation reaction, it may be desirable to employ a solvent. Solvents suitable for use include, in addition to an excess of cyclohexanone, methylene chloride, 1,2-dichloroethane, 1,1,2-trichloro-1,2,2-trifluoroethane, fluorotrichloromethane, 1,2-difluoro-1,1,2,2-tetrachloroethane, acetic acid, ethyl acetate, chlorobenzene, chloroform, toluene, acetonitrile and benzene. Preferred solvents include acetic acid, methylene chloride, chlorobenzene and the chlorofluorocarbons, the latter because of their low flammability and toxicity.

Separation and recovery of the methyl-substituted benzaldehyde and the methyl-substituted benzoic acid from their aforesaid respective reaction mixtures, and further purification thereof if desired, is conveniently accomplished by such well-known conventional procedures as distillation, crystallization, filtration and chromatography. In the process for the preparation of a methyl-substituted benzoic acid using a methyl-substituted benzaldehyde prepared by the first process, purification of the methyl-substituted benzaldehyde is generally unnecessary. For example, a convenient separation process includes addition of water to the formylation reaction mixture to separate aluminum chloride from the aldehyde, separation of the aqueous layer and oxidation of the residual aldehyde solution, with or without first removing the chlorobenzene solvent by distillation.

In order to provide a comparison with the results of Examples 1 and 2, the following experiment was carried out without added chlorobenzene. An inferior yield of less pure mesitaldehyde was obtained.

Mesitylene (75.0 g, 0.625 mol) and aluminum chloride (57.5 g, 0.43 mol) were mixed in a pressure vessel. The vessel was evacuated and 3 g of anhydrous hydrogen chloride were added. The vessel was heated at 50° under 500 psi (3450 kPa) carbon monoxide pressure for 5 hr, after which the reaction mixture was poured onto 250 mL of ice. The organic layer was separated and the aqueous phase was extracted with 100 mL of methylene chloride. The organic layers were combined and then dried (over MgSO$_4$); the solvent was then evaporated off. Distillation of the liquid residue gave 35.2 g (55% yield) of mesitaldehyde, approximately 95% pure as determined by nmr: bp 111°–112° at 20 mm.

In order to provide a comparison with the results of Examples 5, 6, 7 and 8 the following experiment was carried out without added cyclohexanone. An inferior yield of mesitoic acid was obtained.

To a flask equipped with a stirrer, condenser and oxygen inlet tube were added mesitaldehyde (14.8 g, 0.10 mol), 25 mL of chlorobenzene and a solution of 10 mg of cobalt (II) acetate in 1 mL of acetic acid. Oxygen was bubbled in while the solution was vigorously stirred. The reaction temperature rose to 88° in 20 min and then returned to room temperature after one hour. The reaction mixture was mixed with 60 mL of methylene chloride, and 100 mL of water was added. Aqueous potassium hydroxide (40%) was added dropwise until the pH reached 8. The aqueous layer was separated, washed successively with 50 mL of methylene chloride and 50 mL of petroleum ether, and acidified with concentrated hydrochloric acid to a pH of 2. The white solid product was collected by filtration, washed with water and air dried to give 9.82 g (60% yield) of mesitoic acid: mp 153.5°–155.5° C.

The following examples are illustrative of the invention processes; all parts and percentages are by weight and all degrees are Celsius unless otherwise stated.

EXAMPLE 1

Mesitaldehyde

A solution of mesitylene (50.0 g, 0.42 mol) in 200 mL of chlorobenzene was mixed with aluminum chloride (56 g, 0.42 mol) in a pressure vessel. The vessel was evacuated and 11 g of anhydrous hydrogen chloride were added. The pressure was raised to 800–900 psi (5500–6200 kPa) with carbon monoxide; the temperature was maintained at 25°. After 5 hr the reaction mixture was poured onto ice. The entire mixture was acidified and extracted with a total of 400 mL of methylene chloride. The methylene chloride solution was rinsed with water and dried (over MgSO$_4$) and the solvent was removed therefrom at reduced pressure. The residue was distilled under vacuum to give 40.2 g (67% yield) of mesitaldehyde: bp 118°–120° (~25 mm). The ir and nmr spectra confirmed the structure of the product. No detectable impurities were evident by nmr.

EXAMPLE 2

Mesitaldehyde

A solution of mesitylene (100.0 g, 0.833 mol) in 250 mL of chlorobenzene was mixed with aluminum chloride (114 g, 0.84 mol) in a pressure vessel. The vessel was evacuated and 3 g of anhydrous hydrogen chloride were added. The pressure was raised to 300 psi (2060 kPa) with carbon monoxide; the temperature was increased to 50°. After 2 hr (carbon monoxide absorption ceased after 1 hr) the reaction mixture was poured onto 1 L of ice. The organic layer was separated and dried (over MgSO$_4$) and the chlorobenzene was evaporated therefrom at reduced pressure. Distillation of the residue produced 95.3 g (77.2% yield) of mesitaldehyde: bp 114°–116° at 25 mm. No detectable impurities were evident by nmr.

EXAMPLE 3

Pentamethylbenzaldehyde

A solution of pentamethylbenzene (50.0 g, 0.338 mol) in 200 mL of chlorobenzene was mixed with aluminum chloride (50.0 g, 0.375 mol) in a pressure vessel. After evacuation of the vessel 2 g of anhydrous hydrogen chloride were added. The pressure was increased to 600 psi (4150 kPa) with carbon monoxide; the temperature was raised to 50°. After 90 min the reaction mixture was poured into 300 mL of ice water. The organic layer was separated and the aqueous layer was extracted with 100 mL of methylene chloride. The organic layers were combined and then dried (MgSO$_4$); the solvent was evaporated off to give 53.5 g of off-white solid product. Recrystallization of the product from methylene chloride-hexane produced 43.9 g (73.8% yield) of pure white pentamethylbenzaldehyde: mp 148°–150°. No detectable impurities were evident by nmr.

EXAMPLE 4

2,3,4,6-Tetramethylbenzaldehyde

A solution of isodurene (55.0 g, 0.41 mol) in 200 mL of chlorobenzene was mixed with aluminum chloride (60.0 g, 0.45 mol) in a pressure vessel. After evacuation of the vessel 2 g of anhydrous hydrogen chloride were added. After 100 min at 50° under 600 psi (4150 kPa) pressure of carbon monoxide the reaction mixture was poured into 300 mL of ice water. The organic layer was separated and the aqueous layer was extracted with 100 mL of methylene chloride. The organic layers were combined and then dried (over MgSO$_4$); the solvent was evaporated off. Distillation of the liquid residue gave 41.9 g (63% yield) of 2,3,4,6-tetramethylbenzaldehyde (>95% pure as determined by glc): bp 133°–135° at 20 mm. The structure of the product was confirmed by the ir and nmr spectra.

EXAMPLE 5

Mesitoic Acid

To a flask equipped with a stirrer, condenser and an oxygen inlet were added mesitaldehyde (20.0 g, 0.135 mol), 15 mL of chlorobenzene, 15 mL (0.145 mol) of cyclohexanone and 10 mg of cobalt (II) acetate dissolved in 1 mL of acetic acid. Oxygen ws bubbled in slowly while the solution was stirred overnight. The reaction temperature was raised to 50° and the oxidation was continued for an additional 4 hr. The flask was cooled to 0° and the reaction product was removed by filtration and washed with petroleum ether. A total of 12.0 g (55% yield) of crystalline mesitoic acid was obtained. Additional mesitoic acid (2.4 g) was obtained from the filtrate by evaporation, dissolution of the residue in ether, extraction of the ether solution with aqueous sodium bicarbonate and acidification of the aqueous extract. The total yield of product was 65%. The identity of the product was confirmed by its nmr spectrum (CDCl$_3$).

EXAMPLE 6

Mesitoic Acid

To a flask equipped with a stirrer, condenser and an oxygen inlet were added mesitaldehyde (14.8 g, 0.10 mol), 30 mL (0.29 mol) of cyclohexanone and 10 mg of cobalt (II) acetate dissolved in 1 mL of acetic acid. Oxygen was bubbled in while the solution was stirred rapidly. Within an hour the temperature had risen to 70°, then declined rapidly. After 3 hr the solution was mixed with 75 ml of methylene chloride and 100 ml of water. Aqueous potassium hydroxide (40%) was added dropwise until the pH reached 7.5. The aqueous layer was separated and rinsed first with 50 mL of methylene chloride, then with 50 mL of petroleum ether. After acidification with concentrated hydrochloric acid, the white crystalline product was collected by filtration, washed with water and air dried: 12.54 g (77%) of mesitoic acid, mp 154°–156°.

EXAMPLE 7

Mesitoic Acid

To a flask equipped with a stirrer, oxygen inlet and condenser were added mesitaldehyde (10.0 g, 67.6 mmol), 25 mL (0.242 mol) of cyclohexanone and 100 mg of azobisisobutyronitrile. Oxygen was bubbled in while the solution was stirred and maintained at 60°. After 45 hr the solution was mixed with 250 mL of water and 250 mL of methylene chloride; 20% aqueous potassium hydroxide was added dropwise until a pH of 8–9 was reached. The aqueous layer was separated and acidified with concentrated hydrochloric acid, after which the white solid product was collected by filtration, washed with water and air dried: 9.76 g (88% yield) of mesitoic acid.

EXAMPLE 8

Mesitoic Acid

To a flask equipped with a stirrer, oxygen inlet and condenser were added mesitaldehyde (10.0 g, 67.6 mmol), 25 mL (0.242 mol) of cyclohexanone and 100 mg of benzoyl peroxide. Oxygen was bubbled in at fast rate while the stirred solution was maintained at 85°.

After 24 hour an additional 50 mg of benzoyl peroxide was added and the reaction was continued at 90° for an additional 5 hr. After 29 hr total time the solution was mixed with 150 mL of water and 150 mL of methylene chloride; 20% aqueous potassium hydroxide was added dropwise until a pH of 8 was reached. The aqueous layer was separated and acidified with concentrated hydrochloric acid, after which the precipitated product was collected, washed with water and air dried to give 9.74 g (88% yield) of white mesitoic acid: mp 153°–155°.

EXAMPLE 9

2,3,4,6-Tetramethylbenzoic Acid

To a flask equipped with an oxygen inlet, stirrer and condenser were added 2,3,4,6-tetramethylbenzaldehyde (8.10 g, 50 mmol), 20 mL (0.194 mol) of cyclohexanone and 4 mg of cobalt (II) acetate dissolved in several drops of acetic acid. Oxygen was bubbled in while the solution was rapidly stirred. After 2½ hr at room temperature and 4 hr at 50° the solution was poured into a separatory funnel and extracted with 100 mL, then 50 mL, of 3% aqueous sodium bicarbonate solution. The combined aqueous extracts were rinsed with 50 mL of cyclohexane, then acidified to a pH of 2 with concentrated hydrochloric acid and the precipitated product was collected by filtration, washed with water and air dried. A total of 5.2 g (58% yield) of fluffy white 2,3,4,6-tetramethylbenzoic acid was obtained: mp 164°–167°.

EXAMPLE 10

Pentamethylbenzoic Acid

To a flask equipped with a stirrer, oxygen inlet and condenser were added pentamethylbenzaldehyde (12.0 g, 68 mmol), 40 mL (0.387 mol) of cyclohexanone and 6 mg of cobalt (II) acetate dissolved in several drops of acetic acid. Oxygen was bubbled in while the solution was stirred rapidly and heated at 50° for 4 hours. The solution was mixed with 100 mL of cyclohexane and the mixture was extracted with 100 mL of 6% aqueous sodium bicarbonate solution. The aqueous layer was separated and the organic layer was washed with 50 mL of water. The combined aqueous layers were acidified with concentrated hydrochloric acid. The white crystalline solid product was collected by filtration, washed with water and air dried. A total of 10.3 g (78% yield) of pentamethylbenzoic acid was obtained: mp 202°–206°.

Best Mode

The best mode for carrying out the aldehyde preparative process is demonstrated by Example 2. The best mode for carrying out the acid preparative process is demonstrated by Example 6.

Industrial Applicability

Methyl-substituted benzaldehydes and methyl-substituted benzoic acids are well known chemical compounds. Utilities for the aldehydes include usage as fragrances and as intermediates for preparation of the acids and dyestuffs. The acids are commonly used as catalysts for acid-catalyzed polymerization reactions.

I claim:

1. Improved process for preparing a methyl-substituted benzoic acid by oxidizing, in a reaction mixture, at a temperature within the range about 0° to 120° C., the methyl-substituted benzaldehyde of the formula

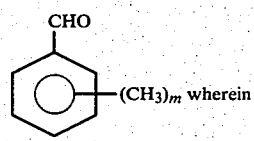

m is 2, 3, 4 or 5, with an excess of oxygen, in the presence of about 0.01 to 2 percent by weight, based on the weight of aldehyde, of an autoxidation initiator, with the methyl-substituted benzoic acid thus produced being separated from the reaction mixture and recovered, the improvement characterized in that the oxidation reaction is carried out in the reaction mixture in the presence of at least 0.5 molar equivalent, per mole of aldehyde, of cyclohexanone as a reductant.

2. Process of claim 1 wherein the amount of cyclohexanone in the reaction mixture is at least 1 molar equivalent per mole of aldehyde.

3. Process of claim 1 wherein the aldehyde is mesitaldehyde and the methyl-substituted benzoic acid is mesitoic acid.

4. Process of claim 1 wherein, upon substantial completion of the reaction, water is added to the reaction mixture to separate aluminum chloride from the aldehyde produced, the aqueous layer thus formed is removed and the residual aldehyde solution is used in the process of claim 5 as a source of the aldehyde.

5. Process of claim 4 wherein chlorobenzene is removed from the residual aldehyde solution before it is used in the process of claim 1.

6. Process of claim 1 wherein the autoxidation initiator is a cobalt salt.

* * * * *